United States Patent
Nappa

(10) Patent No.: US 8,822,739 B2
(45) Date of Patent: Sep. 2, 2014

(54) CATALYTIC ISOMERIZATION OF 2,3,3,3-TETRAFLUOROPROPENE

(71) Applicant: E I du Pont de Nemours and Company, Wilmington, DE (US)

(72) Inventor: Mario Joseph Nappa, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/786,531

(22) Filed: Mar. 6, 2013

(65) Prior Publication Data

US 2013/0253234 A1  Sep. 26, 2013

Related U.S. Application Data

(60) Provisional application No. 61/614,187, filed on Mar. 22, 2012.

(51) Int. Cl.
*C07C 17/358* (2006.01)
*C07C 21/18* (2006.01)
*C07C 21/02* (2006.01)

(52) U.S. Cl.
CPC ............... *C07C 17/358* (2013.01); *C07C 21/02* (2013.01)
USPC ............................ 570/151; 570/236; 570/256

(58) Field of Classification Search
CPC ...................................................... C07C 17/358
USPC ......... 570/151, 156, 236, 123, 166, 153, 256, 570/227
See application file for complete search history.

(56) References Cited

U.S. PATENT DOCUMENTS

| | | | |
|---|---|---|---|
| 2,271,356 A | 1/1942 | Turkevich | |
| 3,258,500 A | 6/1966 | Swamer et al. | |
| 4,828,818 A | 5/1989 | Carlson et al. | |
| 4,902,838 A | 2/1990 | Manzer et al. | |
| 4,978,649 A | 12/1990 | Surovikin et al. | |
| 5,036,036 A | 7/1991 | Lerou | |
| 5,136,113 A | 8/1992 | Rao | |
| 5,157,171 A | 10/1992 | Sievert et al. | |
| 7,420,094 B2 * | 9/2008 | Petrov et al. | 570/151 |
| 7,423,188 B2 | 9/2008 | Miller et al. | |
| 7,722,781 B2 | 5/2010 | Rao et al. | |
| 7,897,823 B2 | 3/2011 | Miller et al. | |
| 2008/0207962 A1 * | 8/2008 | Rao et al. | 570/156 |

OTHER PUBLICATIONS

Quan, SbF5/PAF a novel fluorinating reagent in preparing fluorine compounds, Journal of Fluorine Chemistry, 2004, 125, 1169-1172.
Ruthruff, Inorganic Synthesis, vol. II, Edited by W. Conrad Fernelius, 1946, McGraw-Hill Book Company, Inc.

* cited by examiner

*Primary Examiner* — Fereydoun G Sajjadi
*Assistant Examiner* — Medhanit Bahta

(57) ABSTRACT

An isomerization process is disclosed. The process involves contacting 2,3,3,3-tetrafluoropropene with a suitable catalyst in a reaction zone to produce a product mixture comprising 1,3,3,3-tetrafluoropropene.

13 Claims, No Drawings

CATALYTIC ISOMERIZATION OF 2,3,3,3-TETRAFLUOROPROPENE

BACKGROUND

1. Field of the Disclosure

The present disclosure relates in general to the processes of catalytic isomerization of 2,3,3,3-tetrafluoropropene (HFC-1234yf) to make 1,3,3,3-tetrafluoropropene (HFC-1234ze).

2. Description of Related Art

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs).

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for chemical compounds that do not contribute to the destruction of stratospheric ozone and also have low global warming potentials (GWPs).

BRIEF SUMMARY OF THE DISCLOSURE

The present disclosure provides a process comprising: contacting 2,3,3,3-tetrafluoropropene (HFC-1234yf) with a suitable catalyst in a reaction zone to produce a product mixture comprising 1,3,3,3-tetrafluoropropene (HFC-1234ze).

DETAILED DESCRIPTION

Tetrafluoropropenes, having zero ozone depletion and low global warming potential, have been identified as potential refrigerants and foam expansion agents. However, the toxicity, boiling point, and other physical properties in this class of chemicals varies greatly from isomer to isomer. One tetrafluoropropene having valuable properties is HFC-1234ze. Thus, there is a need for new manufacturing processes for the production of HFC-1234ze.

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Before addressing details of embodiments described below, some terms are defined or clarified.

HFC-1234ze may exist as one of two configurational isomers, E or Z. HFC-1234ze as used herein refers to the isomers, E-HFC-1234ze or Z-HFC-1234ze, as well as any combinations or mixtures of such isomers.

The term "isomerization process", as used herein, means the process during which HFC-1234yf is isomerized to form HFC-1234ze.

The term "hydrofluorocarbon", as used herein, means a molecule containing hydrogen, carbon, and fluorine. A hydrofluorocarbon in this disclosure can be saturated or unsaturated.

The term "chlorofluorocarbon", as used herein, means a molecule containing chlorine, carbon, and fluorine.

The term "an elevated temperature", as used herein, means a temperature higher than the room temperature.

The term "amorphous", as used herein, means that there is no substantial peak in a X-ray diffraction pattern of the subject solid.

The term "isomerization yield", as used herein, means the molar percentage of the amount of HFC-1234ze formed in the process compared to the amount of starting material HFC-1234yf.

The present disclosure provides an isomerization process which comprises contacting HFC-1234yf with a suitable catalyst in a reaction zone to produce a product mixture comprising HFC-1234ze. During the process, HFC-1234yf is isomerized to form HFC-1234ze. This isomerization process can be carried out in the liquid phase or vapor phase using well-known chemical engineering practice, which includes continuous, semi-continuous or batch operations.

In some embodiments of this invention, the suitable catalyst comprises chromium. In some embodiments of this invention, the suitable catalyst comprises chromium oxyfluoride which can be represented by formula $Cr_2O_xF_y$, wherein $x+y/2=3$. Typically, a chromium oxyfluoride catalyst is used in a vapor phase isomerization process.

The chromium oxyfluoride catalysts can be prepared by treating chromium oxide ($Cr_2O_3$) with a fluorinating agent such as HF, $CCl_3F$, $COF_2$ or hydrofluorocarbons. In some embodiments of this invention, a chromium oxyfluoride catalyst is prepared by treating dry $Cr_2O_3$ with a fluorinating agent such as $CCl_3F$ or HF. This treatment can be accomplished by placing $Cr_2O_3$ in a suitable container (which can be the reactor to be used to perform the subsequent isomerization reaction) and thereafter passing HF over the dry $Cr_2O_3$ for a suitable period of time (e.g., about 15 to 300 minutes) at a suitable temperature (e.g., about 200° C. to 450° C.), such as what described in Example 1.

In some embodiments of this invention, a chromium oxyfluoride catalyst is prepared by treating $Cr_2O_3$ with a hydrofluorocarbon at an elevated temperature.

In some embodiments of this invention, a chromium oxyfluoride catalyst is made in situ. For example, the starting material HFC-1234yf can be employed in the formation of a chromium oxyfluoride catalyst by heating together with $Cr_2O_3$ in the reactor.

$Cr_2O_3$ is commercially available from BASF Catalysts LLC, 25 Middlesex Essex Turnpike, Iselin, N.J. 08830-0770.

$Cr_2O_3$ can also be prepared by reducing chromium (VI) oxide in water with a suitable reducing agent, such as ethanol, as disclosed in U.S. Pat. No. 3,258,500, which is incorporated herein by reference. Of note is the so-called gel-type activated $Cr_2O_3$ obtained by reducing chromium trioxide ($CrO_3$) and dehydrating the reduced product in the manner disclosed by Ruthruff in "Inorganic Synthesis", Vol. II, pp. 190-193, published in 1946 by McGraw-Hill Book Co., New York, and by Turkevich and Ruthruff in U.S. Pat. No. 2,271,356, both of which are incorporated herein by reference. In one embodiment of this invention, $Cr_2O_3$ is prepared by dissolving chromium trioxide in water, gradually adding ethanol or other suitable reducing agent to the solution and heating under reflux conditions until the $Cr_2O_3$ gel precipitates, separating the gel from the reaction mixture, drying it, and then dehydrating and activating the product by heating it at a temperature of from about 400° C. to about 600° C. in an inert atmosphere until the water is removed and an anhydrous product is obtained.

$Cr_2O_3$ can also be prepared by pyrolysis of ammonium dichromate (($NH_4$)$_2Cr_2O_7$) as disclosed in U.S. Pat. No. 5,036,036, which is incorporated herein by reference. Of note is $Cr_2O_3$ prepared by pyrolysing ammonium dichromate and treating (e.g., washing with deionized water) the resulting $Cr_2O_3$ to reduce the alkali metal content to 100 ppm or less. Also of note is $Cr_2O_3$ prepared by first treating ammonium dichromate containing 60-2000 ppm alkali metal to reduce its alkali metal content to less than 60 ppm and then pyrolysing the resulting ammonium dichromate with reduced alkali metal content to form $Cr_2O_3$ containing 100 ppm or less of alkali metal content.

$Cr_2O_3$ can also be prepared by the reaction of chromium (VI) oxide with a reducing solvent, such as methanol, as disclosed in U.S. Pat. No. 4,828,818, which is incorporated herein by reference.

The amount of potassium and other alkali metals in $Cr_2O_3$ can be reduced by a water washing step as disclosed in U.S. Pat. No. 5,036,036, which is incorporated herein by reference. In some embodiments of this invention, the water washing step includes forming a slurry containing 5-15 wt % $Cr_2O_3$ and deionized water. Stirring of this water slurry can be carried out at 35° C. to 65° C. for at least one hour, and in some embodiments for two or more hours. The solids are then recovered by filtration, suitably on a plate and frame filter press. The filter cake can be analyzed for alkali metal content. The washing step can be repeated to obtain a desired level of alkali metal content.

In some embodiments of this invention, the chromium oxyfluoride catalyst has surface areas of about 20 $m^2/g$ to about 500 $m^2/g$.

In some embodiments of this invention, the chromium oxyfluoride catalyst has surface areas of about 40 $m^2/g$ to about 350 $m^2/g$.

In some embodiments of this invention, the chromium oxyfluoride catalyst has surface areas of about 60 $m^2/g$ to about 300 $m^2/g$.

In some embodiments of this invention, the chromium oxyfluoride catalyst has surface areas of about 100 $m^2/g$ to about 300 $m^2/g$.

In some embodiments of this invention, the chromium oxyfluoride catalyst contains an alkali metal content of about 2000 ppm or less.

In some embodiments of this invention, the chromium oxyfluoride catalyst contains an alkali metal content of about 300 ppm or less.

In some embodiments of this invention, the chromium oxyfluoride catalyst contains an alkali metal content of about 100 ppm or less.

In some embodiments of this invention, the chromium oxyfluoride catalyst is amorphous.

In some embodiments of this invention, the chromium oxyfluoride catalyst is prepared from crystalline $\alpha$-$Cr_2O_3$.

The form of the catalyst is not critical and may be used as pellets, powders or granules.

In some embodiments of this invention, the suitable catalyst comprises a transition metal modified chromium oxide or a transition metal modified chromium oxyfluoride. Typically, a transition metal modified chromium oxide catalyst or a transition metal modified chromium oxyfluoride catalyst is used in a vapor phase isomerization process. In some embodiments of this invention, such transition metal is selected from the group consisting of magnesium (e.g. magnesium fluoride), Group VIIB metals (e.g., manganese), Group IIIB metals (e.g., lanthanum), and zinc. In use, such transition metals are normally present as halides (e.g., fluorides), as oxides and/or as oxyhalides. In some embodiments of this invention, these transition metals are supported on chromium oxide or chromium oxyfluoride.

In the embodiments wherein a chromium oxyfluoride, a transition metal modified chromium oxide, or a transition metal modified chromium oxyfluoride is used as the catalyst for the vapor phase isomerization process, the contact time of the starting material HFC-1234yf with the catalyst can vary widely depending on the degree of conversion desired and generally will be from about 1 second to about 1000 seconds. In some embodiments of the invention, the contact time ranges from about 10 seconds to about 200 seconds. The temperature employed in the reaction zone of the isomerization process typically ranges from about 150° C. to 500° C. In some embodiments of the invention, the temperature employed in the reaction zone of the isomerization process ranges from about 300° C. to 400° C. The reaction zone pressure for the isomerization process can be subatmospheric, atmospheric or superatmospheric. In some embodiments of the invention, the reaction zone pressure can be up to 200 psi. In some embodiments of the invention, the reaction zone pressure is near atmospheric. Optionally, such isomerization process can be conducted in the presence of oxygen. In one embodiment of the invention, such isomerization process can be conducted in the presence of air. In another embodiment of the invention, air is co-fed with the starting material HFC-1234yf into the reaction zone.

In some embodiments of this invention, the suitable catalyst is selected from the group consisting of alumina, fluorided alumina, aluminum fluoride and mixtures thereof. Typically, such suitable catalyst is used in a vapor phase isomerization process.

In some embodiments of this invention, the suitable catalyst is selected from the group consisting of transition metal modified alumina, transition metal modified fluorided alumina, transition metal modified aluminum fluoride and mixtures thereof. Typically, such suitable catalyst is used in a vapor phase isomerization process. In some embodiments of this invention, the transition metal is selected from the group consisting of magnesium (e.g. magnesium fluoride), Group VIIB metals (e.g., manganese), Group IIIB metals (e.g., lanthanum), and zinc. In use, such transition metals are normally present as halides (e.g., fluorides), as oxides and/or as oxyhalides. In some embodiments of this invention, these transition metals are supported on alumina, fluorided alumina, or aluminum fluoride. Fluorided alumina and aluminum fluoride can be prepared as described in U.S. Pat. No. 4,902,838, herein incorporated by reference.

In the vapor phase embodiments wherein the suitable catalyst is selected from the group consisting of alumina, fluorided alumina, aluminum fluoride and mixtures thereof, and in the vapor phase embodiments wherein the suitable catalyst is selected from the group consisting of transition metal modified alumina, transition metal modified fluorided alumina, transition metal modified aluminum fluoride and mixtures thereof, the contact time of the starting material HFC-1234yf with the catalyst can vary widely depending on the degree of conversion desired and generally will be from about 1 second to about 1000 seconds. In some embodiments of the invention, the contact time ranges from about 10 seconds to about 200 seconds. The temperature employed in the reaction zone of the isomerization process typically ranges from about 150° C. to 500° C. In some embodiments of the invention, the temperature employed in the reaction zone of the isomerization process ranges from about 300° C. to 400° C. The reaction zone pressure for the isomerization process can be subatmospheric, atmospheric or superatmospheric. In some embodiments of the invention, the reaction zone pressure can be up to 200 psi. In some embodiments of the invention, the reaction zone pressure is near atmospheric. Optionally, such isomerization process can be conducted in the presence of oxygen. In one embodiment of the invention, such isomerization process can be conducted in the presence of air. In another embodiment of the invention, air is co-fed with the starting material HFC-1234yf into the reaction zone.

In some embodiments of this invention, the suitable catalyst comprises aluminum chlorofluoride which can be represented by formula $AlCl_{3-m}F_m$ wherein m is from about 1.0 to less than 3. The aluminum chlorofluoride catalyst can be used in a vapor phase or a liquid phase isomerization process.

Aluminum chlorofluoride can be prepared by reacting commercially available anhydrous $AlCl_3$ with one or more saturated chlorofluorocarbons as disclosed in U.S. Pat. No. 5,157,171 to Sievert, et al., which is incorporated herein by reference. By way of explanation, the aluminum chlorofluoride catalysts used in the isomerization process are prepared by treating anhydrous aluminum chloride with an excess of saturated chlorofluorocarbons such as $CCl_3F$, $CCl_2F_2$, $CCl_2FCCl_2F$, $CCl_2FCClF_2$, $CClF_2CClF_2$, $CCl_2FCCl_3$, $CCl_2FCCl_3$, $CF_3CCl_3$, $CF_3CCl_2F$, and $CF_3CClF_2$; preferably $CCl_3F$, $CCl_2F_2$, $CCl_2FCCl_2F$, $CCl_2FCClF_2$, and $CClF_2CClF_2$; and most preferably $CCl_3F$. It is believed that propane derivatives displaying the structural features shown above may also be used in the process of preparing the aluminum chlorofluoride catalysts. The reaction between aluminum chloride and the saturated chlorofluorocarbons occurs, for the most part, spontaneously, and is exothermic. In certain instances, such as with $C_2$ saturated chlorofluorocarbons, slight heating may be used advantageously. For compounds containing —$CF_3$ groups such as $CCl_3CF_3$, more vigorous conditions are required to effect reaction with $AlCl_3$, and the reaction is best carried out under the pressure developed autogenously by the reactants. After the reaction has subsided, the liquid products are removed, generally under reduced pressures to provide an aluminum chlorofluoride catalyst which will usually contain from about 3 to about 68% fluorine by weight. The liquid product from the reaction of saturated chlorofluorocarbons with $AlCl_3$ includes products which are produced by halogen exchange reaction with the aluminum chloride as well as rearranged saturated chlorofluorocarbons.

The solid aluminum chlorofluoride product of the reaction of $AlCl_3$ with saturated chlorofluorocarbons may be separated from the liquid products by filtration, by distillation or vacuum transfer of the liquid products from the aluminum chlorofluoride, or, alternatively, the aluminum chlorofluoride catalyst may be used as a suspension for subsequent isomerization reactions.

In the embodiments wherein an aluminum chlorofluoride is used as the catalyst for the vapor phase or liquid phase isomerization process, the reaction zone temperature typically ranges from about −20° C. to about 150° C. In some embodiments of the invention, the reaction zone temperature ranges from about −10° C. to about 100° C. In some embodiments of the invention, the reaction zone temperature ranges from about 0° C. to about 50° C. In some embodiments of the invention, the reaction zone temperature is about ambient, i.e., room temperature. The reaction zone pressure for the isomerization process can be subatmospheric, atmospheric or superatmospheric. In some embodiments of the invention, the reaction zone pressure is near atmospheric.

In some embodiments of this invention, the suitable catalyst comprises $SbCl_{5-n}F_n$ wherein n is from 1 to 5. Typically, such catalyst is used in a liquid phase isomerization process.

In some embodiments of this invention, the suitable catalyst comprises $SbCl_{5-n}F_n$ supported on $AlF_3$ or carbon. Typically, such catalyst is used in a vapor phase isomerization process.

$AlF_3$ can be made according to Journal of Fluorine Chemistry, 125, 1169-1172 (2004), which is incorporated herein by reference.

Carbon used in the embodiments of this invention may come from any of the following sources: wood, peat, coal, coconut shells, bones, lignite, petroleum-based residues and sugar. Commercially available carbons which may be used include those sold under the following trademarks: Barneby & Sutcliffe™, Darco™, Nucharm™, Columbia JXN™, Columbia LCK™, Calgon™ PCB, Calgon™ BPL, Westvaco™, Norit™, Takeda™ and Barnaby Cheny NB™.

The carbon also includes three dimensional matrix porous carbonaceous materials. Examples are those described in U.S. Pat. No. 4,978,649. In one embodiment of the invention, carbon includes three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

Embodiments of carbon include both non-acid washed and acid-washed carbons. In some embodiments of this invention, carbon may be prepared by treating the carbon with acids such as $HNO_3$, HCl, HF, $H_2SO_4$, $HClO_4$, $CH_3COOH$, and combinations thereof. Acid treatment is typically sufficient to provide carbon that contains less than 1000 ppm of ash. Some suitable acid treatments of carbon are described in U.S. Pat. No. 5,136,113.

In some embodiments of this invention, carbon is an activated carbon. In some embodiments of this invention, carbon is a non-acid washed activated carbon. In some embodiments of this invention, carbon is an acid washed activated carbon. The carbon can be in the form of powder, granules, or pellets, et al.

Preparation of $SbF_5$ on $AlF_3$ has been described by Quan et al. in Journal of Fluorine Chemistry, 125, 1169-1172 (2004).

Preparation of $SbCl_{5-n}F_n$ on $AlF_3$ is generally described in Example 4.

The isomerization process in the presence of $SbCl_{5-n}F_n$ is typically carried out in anhydrous or substantially anhydrous conditions, which means that water, which is detrimental to the reaction, should be excluded as much as possible from the reaction zone.

In the embodiments wherein a $SbCl_{5-n}F_n$ catalyst ($SbCl_{5-n}F_n$, or $SbCl_{5-n}F_n$ supported on $AlF_3$ or carbon) is used for the isomerization processes, the reaction zone temperature typically ranges from about −20° C. to about 150° C. In some embodiments of the invention, the reaction zone temperature ranges from about −10° C. to about 100° C. In some embodiments of the invention, the reaction zone temperature ranges from about 0° C. to about 50° C. In some embodiments of the invention, the reaction zone temperature is about ambient, i.e., room temperature. The reaction zone pressure for the isomerization process can be subatmospheric, atmospheric or superatmospheric. In some embodiments of the invention, the reaction zone pressure is near atmospheric.

The isomerization process of this disclosure may be conducted by methods known in the art. In some embodiments of this invention, the HFC-1234yf starting material is fed to a reactor containing the suitable catalyst. In some embodiments of this invention, the HFC-1234yf starting material is passed through a catalyst bed in a reactor.

The effluent from the reaction zone is typically a product mixture comprising unreacted starting material HFC-1234yf, the desired product HFC-1234ze, and some byproducts such as HFC-236fa ($CF_3CH_2CF_3$) and HFC-245fa ($CHF_2CH_2CF_3$). HFC-1234ze may be recovered from the product mixture by conventional methods. In some embodiments of this invention, HFC-1234ze may be purified or recovered by distillation. In some embodiments of this invention, the unreacted starting material HFC-1234yf are recovered and recycled back to the reaction zone.

In some embodiments of this invention, isomerization yield of HFC-1234ze is at least 70 mole %. In some embodiments of this invention, isomerization yield of HFC-1234ze is at least 85 mole %.

In some embodiments of this invention, HFC-1234ze present in the product mixture may be separated from the other components of the product mixture by fractional distillation.

In some embodiments of this invention, HF is added to the product mixture, and separation of HFC-1234ze includes isolation of azeotrope or near azeotrope of HFC-1234ze and HF and further processing to produce HF-free HFC-1234ze by using procedures similar to that disclosed in U.S. Pat. No. 7,722,781 and U.S. Pat. No. 7,423,188, both herein incorporated by reference.

Unreacted HFC-1234yf can be separated and recycled to the reactor for the production of additional HFC-1234ze.

In some embodiments of this invention, unreacted HFC-1234yf present in the product mixture may be separated from the other components of the product mixture by fractional distillation.

In some embodiments of this invention, HF is added to the product mixture, and separation of unreacted HFC-1234yf includes isolation of azeotrope or near azeotrope of HFC-1234yf and HF and further processing to produce HF-free HFC-1234yf by using procedures similar to that disclosed in U.S. Pat. No. 7,897,823, herein incorporated by reference.

The reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Legend

| | |
|---|---|
| HFC-1234ze is $CF_3CH=CHF$ | HFC-1234yf is $CF3CF=CH2$ |
| HFC-236fa is $CF_3CH_2CF_3$ | HFC-245fa is $CHF_2CH_2CF_3$ |

Example 1

This example is prophetic. Chromium oxide used in this example is synthesized according to the process described in U.S. Pat. No. 3,258,500 from the reduction of chromium trioxide. This form of chromium oxide is usually amorphous and has a surface area in excess of 180 m²/gm.

An Inconel tube (⅝ inch OD) is filled with 6 cc (7.12 gm) of chromium oxide gel pellets, crushed and sieved to 12/20 mesh. The catalyst is heated to 200° C. for 15 minutes under a purge of $N_2$ (50 sccm, $8.33 \times 10^{-7}$ m³/s). Then the temperature is raised to 325° C. for 10 minutes, to 400° C. for 20 minutes, and lowered to 300° C. for 35 minutes. The temperature is raised to 325° C. for 60 minutes while flowing $N_2$ (35 sccm, $5.83 \times 10^{-7}$ m³/s) and HF (12 sccm, $2.00 \times 10^{-7}$ m³/s) for 35 minutes. While maintaining this flow, the temperature is raised to 350° C. for 60 minutes, 375° C. for 90 minutes, 400° C. for 30 minutes, and 425° C. for 40 minutes. The flow of $N_2$ is reduced to 25 sccm ($4.17 \times 10^{-7}$ m³/s) and HF raised to 20 sccm ($3.33 \times 10^{-7}$ m³/s) for 20 minutes. Then the flow of $N_2$ is reduced to 15 sccm ($2.50 \times 10^{-7}$ m³/s) and HF raised to 28 sccm ($4.67 \times 10^{-7}$ m³/s) for 20 minutes. Then the flow of $N_2$ is reduced to 5 sccm ($8.33 \times 10^{-8}$ m³/s) and HF raised to 36 sccm ($6.00 \times 10^{-7}$ m³/s) for 20 minutes. Finally, the $N_2$ is shut off and the HF flow is raised to 40 sccm ($6.67 \times 10^{-7}$ m$^3$/s) for 20 minutes and then the temperature is reduced to the reaction temperature.

The temperature of the catalyst bed is set to 350° C. and HFC-1234yf (2,3,3,3-tetrafluoropropene) is flowed through the reactor at 6 sccm ($1.00 \times 10^{-7}$ m$^3$/s). The product mixture effluent is analyzed by both GC-MS and NMR and found to have the following composition: (analytical results are given in units of GC area %) 8% Z-HFC-1234ze, 75% E-HFC-1234ze, 2% HFC-236fa, 3% HFC-245fa, and 12% HFC-1234yf.

Example 2

This example is prophetic. All the other conditions are the same as in Example 1. The temperature of the catalyst bed is set to 400° C. and HFC-1234yf is flowed through the reactor at 6 sccm ($1.00 \times 10^{-7}$ m$^3$/s). The product mixture effluent is analyzed by both GC-MS and NMR and found to have the following composition: (analytical results are given in units of GC area %) 7% Z-HFC-1234ze, 78% E-HFC-1234ze, 2% HFC-236fa, 3% HFC-245fa, and 10% HFC-1234yf.

Example 3

This example is prophetic. In this example, a chromium oxyfluoride catalyst of high surface area is used as described in U.S. Pat. No. 4,828,818. This is an aerogel catalyst with a high surface area, typically greater than 400 m$^2$/gm. An inconel tube (⅝ inch OD) is filled with 6 cc (0.38 gm) of chromium oxide gel particles, crushed and sieved to 12/20 mesh. The catalyst is heated to 200° C. for 15 minutes under a purge of N$_2$ (50 sccm, $8.33 \times 10^{-7}$ m$^3$/s). Then the temperature is raised to 325° C. for 10 minutes, to 400° C. for 20 minutes, and lowered to 300° C. for 35 minutes. The temperature is raised to 325° C. for 60 minutes while flowing N$_2$ (35 sccm, $5.83 \times 10^{-7}$ m$^3$/s) and HF (12 sccm, $2.00 \times 10^{-7}$ m$^3$/s) for 35 minutes. While maintaining this flow, the temperature is raised to 350° C. for 60 minutes, 375° C. for 90 minutes, 400° C. for 30 minutes, and 425° C. for 40 minutes. The flow of N$_2$ is reduced to 25 sccm ($4.17 \times 10^{-7}$ m$^3$/s) and HF raised to 20 sccm ($3.33 \times 10^{-7}$ m$^3$/s) for 20 minutes. Then the flow of N$_2$ is reduced to 15 sccm ($2.50 \times 10^{-7}$ m$^3$/s) and HF raised to 28 sccm ($4.67 \times 10^{-7}$ m$^3$/s) for 20 minutes. Then the flow of N$_2$ is reduced to 5 sccm ($8.33 \times 10^{-8}$ m$^3$/s) and HF raised to 36 sccm ($6.00 \times 10^{-7}$ m$^3$/s) for 20 minutes. Finally, the N$_2$ is shut off and the HF flow is raised to 40 sccm ($6.67 \times 10^{-7}$ m$^3$/s) for 20 minutes and then the temperature is reduced to the reaction temperature.

The temperature of the catalyst bed is set to 350° C. and HFC-1234yf is flowed through the reactor at 6 sccm ($1.00 \times 10^{-7}$ m$^3$/s). The product mixture effluent is analyzed by both GC-MS and NMR and found to have the following composition: (analytical results are given in units of GC area %) 10% Z-HFC-1234ze, 77% E-HFC-1234ze, 2% HFC-236fa, 2% HFC-245fa, and 9% HFC-1234yf.

Example 4

This example is prophetic. Example 4 demonstrates the preparation of SbCl$_{5-n}$F$_n$ (n=1 to 5) on AlF$_3$. Twenty five grams of AlF$_3$.3H$_2$O (12/20 mesh) is heated for 10 hours at 300° C. under a purge of nitrogen (10 sccm, $1.7 \times 10^{-7}$ m$^3$/s). Under an inert atmosphere, the AlF$_3$ is transferred to a glass round bottom flask and 25 gm of SbCl$_5$ is slowly dripped onto the powder. Periodic mixing with a Teflon® paddle is carried out to infuse the mixture. Under an inert atmosphere, the SbCl$_5$ on AlF$_3$ is transferred to ⅝" Inconel tube for treatment with HF. The catalyst is heated under a flow of nitrogen (20 sccm, $3.3 \times 10^{-7}$ m$^3$/s) for three hours at 100° C. Anhydrous HF (50 sccm, $6.0 \times 10^{-7}$ m$^3$/s) and N$_2$ (50 sccm, $6.0 \times 10^{-7}$ m$^3$/s) are passed over the catalyst at 200° C. for 2 hours and then only HF (100 sccm, $1.2 \times 10^{-6}$ m$^3$/s) for 3 hours. The temperature is lowered to ambient and N$_2$ (50 sccm, $6.0 \times 10^{-7}$ m$^3$/s) is passed over the catalyst for 8 hours.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A process comprising: contacting 2,3,3,3-tetrafluoropropene with a suitable catalyst in a reaction zone to produce a product mixture comprising 1,3,3,3-tetrafluoropropene.

2. The process of claim 1 wherein said suitable catalyst comprises chromium oxyfluoride.

3. The process of claim 2 wherein said chromium oxyfluoride is prepared by treating chromium oxide with a fluorinating agent.

4. The process of claim 3 wherein said fluorinating agent is selected from the group consisting of HF, CCl$_3$F and hydrofluorocarbons.

5. The process of claim 1 wherein said suitable catalyst comprises a transition metal modified chromium oxide or a transition metal modified chromium oxyfluoride.

6. The process of claim 5 wherein said transition metal is selected from the group consisting of magnesium, Group VIIB metals, Group IIIB metals, and zinc.

7. The process of claim 6 wherein said transition metal is supported on chromium oxide or chromium oxyfluoride.

8. The process of claim 1 wherein said suitable catalyst is selected from the group consisting of alumina, fluorided alumina, aluminum fluoride and mixtures thereof.

9. The process of claim 8 wherein said suitable catalyst is selected from the group consisting of transition metal modified alumina, transition metal modified fluorided alumina, transition metal modified aluminum fluoride and mixtures thereof.

10. The process of claim 9 wherein said transition metal is selected from the group consisting of magnesium, Group VIIB metals, Group IIIB metals, and zinc.

11. The process of claim 10 wherein said transition metal is supported on alumina, fluorided alumina or aluminum fluoride.

12. The process of claim 1 wherein the isomerization yield of 1,3,3,3-tetrafluoropropene is at least 70 mole %.

13. The process of claim 1 wherein the isomerization yield of 1,3,3,3-tetrafluoropropene is at least 85 mole %.

* * * * *